United States Patent [19]

Joyce

[11] Patent Number: 5,453,832
[45] Date of Patent: Sep. 26, 1995

[54] TURBIDITY MEASUREMENT

[75] Inventor: John G. Joyce, Hants, Great Britain

[73] Assignee: Alfa Laval Separation Inc., Warminster, Pa.

[21] Appl. No.: 920,588

[22] PCT Filed: Mar. 6, 1991

[86] PCT No.: PCT/GB91/00354

§ 371 Date: Aug. 24, 1992

§ 102(e) Date: Aug. 24, 1992

[87] PCT Pub. No.: WO91/14171

PCT Pub. Date: Sep. 19, 1991

[30] Foreign Application Priority Data

Mar. 6, 1990 [GB] United Kingdom .................. 9005021

[51] Int. Cl.$^6$ ........................ G01N 21/26; G01N 15/07
[52] U.S. Cl. ........................ 356/338; 356/342; 250/574
[58] Field of Search ........................ 356/336, 338, 356/339, 342, 343, 440, 441, 442, 244, 246, 445, 446; 250/574, 576; 359/507, 509, 512, 514

[56] References Cited

U.S. PATENT DOCUMENTS

| | | |
|---|---|---|
| 2,569,127 | 9/1951 | Eltenton . |
| 3,163,767 | 12/1964 | Witt et al. . |
| 3,263,553 | 8/1966 | Baruch . |
| 3,639,770 | 2/1972 | Zizelmann . |
| 3,714,444 | 1/1973 | Carr et al. . |
| 3,731,091 | 5/1973 | Rosso et al. . |
| 3,990,795 | 11/1976 | Parker . |
| 4,006,988 | 2/1977 | Tamm . |
| 4,021,120 | 5/1977 | Muller et al. ........................ 356/442 |
| 4,114,038 | 9/1978 | Parker . |
| 4,140,395 | 2/1979 | Kreikebaum ........................ 356/336 |
| 4,155,651 | 5/1979 | Malone . |
| 4,232,967 | 11/1979 | Grachev et al. . |
| 4,274,745 | 6/1981 | Takahashi et al. . |
| 4,451,152 | 5/1984 | Topol et al. ........................ 356/440 |
| 4,561,779 | 12/1985 | Nagamune et al. . |
| 4,659,218 | 4/1987 | de Lasa et al. . |
| 4,672,218 | 6/1987 | Chrisman et al. . |
| 4,725,148 | 2/1988 | Endo et al. . |
| 4,797,550 | 1/1989 | Nelson et al. . |
| 4,797,559 | 1/1989 | Oblad et al. . |
| 4,801,204 | 1/1989 | Nakamura et al. ........................ 356/338 |
| 4,841,157 | 6/1989 | Downing, Jr. ........................ 356/342 |
| 4,843,248 | 6/1989 | Miyata et al. . |
| 4,848,905 | 7/1989 | Iino . |
| 4,874,243 | 10/1989 | Perren . |
| 4,914,310 | 4/1990 | Jarofski . |
| 4,950,908 | 8/1990 | Oblad et al. . |

FOREIGN PATENT DOCUMENTS

| | | |
|---|---|---|
| 0114408 | 8/1984 | European Pat. Off. . |
| 0126031 | 11/1984 | European Pat. Off. . |
| 2299636 | 8/1976 | France . |
| 56-43535 | 4/1981 | Japan . |
| 970148 | of 1964 | United Kingdom . |
| 1281342 | 7/1972 | United Kingdom . |
| 1554834 | 10/1979 | United Kingdom . |
| WO82/03460 | 10/1982 | WIPO . |

*Primary Examiner*—Hoa Q. Pham
*Attorney, Agent, or Firm*—Seidel Gonda Lavorgna & Monaco

[57] ABSTRACT

In measuring the turbidity of a liquid, especially for determining water clarity in a water purification process in which after the addition of flocculant the water is centrifuged, light is emitted as a diffuse beam from a light source and the intensity of light reflected from gas bubbles in the liquid is detected by a photosensor. The light source and photosensor are incorporated in a probe having transparent cylindrical wall. The probe is sealed within a housing confining a liquid receiving chamber. A plurality of seals are provided forming a space containing a cleaning solution. An actuator is coupled to the probe for reciprocating the probe relative to the housing and seals for cleaning deposits from the wall.

29 Claims, 1 Drawing Sheet

TURBIDITY MEASUREMENT

FIELD OF THE INVENTION

This invention is concerned with turbidity measurement, especially but not necessarily exclusively with a view to optimising the consumption of flocculating agent in the treatment of waste-water.

BACKGROUND OF THE INVENTION

It is usual in sewage treatment plants for a flocculant to be added to water which is subsequently centrifuged, e.g. by means of a decanter centrifuge, for removing the coagulated particulate contaminants from the water. The flocculating agents commonly used, such as polyelectrolyte flocculants, are expensive and make a significant contribution to the total water treatment costs. It is necessary for sufficient flocculant to be added to the effluent so that the water is clarified to the level required, but any more than the optimum amount of flocculant means unnecessary additional expense and hence uneconomic operation of the plant. It is known to monitor the quality of the clarified water by making turbidity measurements, and to adjust the rate of consumption of flocculating agent in accordance with the results obtained. While the theory behind this technique for controlling the water purification process is very sound, it has not been possible to implement it effectively because of the limitations imposed and by and suffered by commercially available turbidity meters. Although there are many turbidity meters of various types on the market, none have proved entirely satisfactory for monitoring a clarified liquid stream discharged from a decanter centrifuge in an effluent purification process, and only limited success has been achieved with such meters.

It is well known to measure the turbidity of a liquid by measuring the intensity or attenuation of light transmitted through a sample of the liquid. It has also been proposed to do so by measuring the light scattered and/or reflected from solid particles present in the liquid. In the former method a diminishing signal, which signal indicates the intensity or amount of transmitted light, denotes an increase in the suspended solid particles present, i.e. the turbidity of the liquid, whereas in the latter method an increase in the amount of light detected indicates more particles are present. If the light reflected from the particles is relied upon to provide a measurement, as proposed in GB 1281342, the device will have a very poor response unless the particles are white, or at least very light in colour, assuming visible light is used by the sensor. There is described in WO82/03460 a turbidity meter with a probe consisting of a bundle of optic fibres, some of which are used to emit light and others of which are used to detect the reflected light, but the device is specifically adapted for turbidity measurements on substantially opaque highly turbid liquids, e.g. to determine the butterfat content of milk, and therefore it utilises only a very small sample of liquid immediately in front of the probe.

The reasons why turbidity meters have so far failed to give satisfactory results in their practical application to effluent treatment as mentioned above are several and various. In some cases the range of measurement is wrong or is too narrow; blockage problems are sometimes experienced, particularly where liquid flow passages are small; lens contamination occurs necessitating frequent cleaning operations; or they simply do not give readings reliable enough to enable effective control over the flocculant consumption. One reason for unreliable results is that gas or air bubbles are detected as if they were solid particles. An affect frequently caused by over flocculation is aeration of the clarified water leaving the decanter centrifuge, with the result that numerous bubbles are present and the liquid has a tendency to foam. With bubbles being seen as if they were particles the reading from the turbidity meter can be very misleading to the extent that it suggests more rather than less flocculant needs to be added upstream of the centrifuge. Because of these difficulties it has become accepted practice in the art of waste water treatment to subject the clarified liquid to a de-aeration treatment before passing it to the turbidity meter. In addition, to alleviate the problems associated with precipitation on the lens and thereby reduce the frequency of cleaning operations, it is normal practice to dilute the de-aerated sample before admitting it to the turbidity meter.

From the point of view of making accurate measurements, dilution is disadvantageous since allowance must be made for the effect of the dilution on the actual turbidity of the initial sample. Added to that, both de-aeration and dilution are inconvenient because they are extra steps which must be performed in the water treatment process.

The present invention addresses the problems associated with known turbidity measuring equipment as explained above, and is based on the realisation that the presence of gas bubbles in the liquid sample can be taken advantage of to produce more reliable measurement of turbidity, at least in as much that greater sensitivity to fluctuations in turbidity is possible.

SUMMARY OF THE INVENTION

In accordance with one aspect the invention provides a method of determining the turbidity of a liquid sample containing solid particles, wherein light rays are emitted into the liquid sample and light reflected within the liquid sample is detected, characterised in that the liquid contains gas bubbles in an amount which varies inversely with the concentration of solid particles, and the intensity of light reflected from the gas bubbles is detected.

The wavelength of the light used in performing the method is unimportant, but in the case of clarified effluent water it is convenient to use visible light. In other cases a wavelength outside the visible range may be desirable.

The light is preferably emitted into the liquid as a diffuse beam. For example, in a preferred embodiment the light is emitted from and detected at respective positions located along an axis, the light being emitted into the liquid in all radial directions about said axis, and also being received from the liquid in all radial directions at the detection position. A diffuse beam has the advantage that risk of an incorrect signal as a result of an oversize piece of solid material entering the chamber is diminished due to a large volume of liquid sample being used for measurement purposes. In addition, large transmission window areas through which light passes into and from the liquid assists in reducing errors due to fouling of the window surfaces.

The invention recognises the correlation between the bubble density and the particle concentration in the clarified liquid discharged from a decanter centrifuge in a water purification process. In particular, if less than the optimum amount of flocculant has been added to the water being treated, the particle concentration rises and the degree of aeration, and hence the number of bubbles present in the water diminishes. Conversely, more than the optimum amount of flocculant means a reduction in the particle concentration and greater aeration and more bubbles in the water. Using the method according to the invention to measure turbidity, both the particle concentration and the bubble concentration will influence the amount of reflected light received by the light sensing means, and more importantly they enhance each other (rather than tending to cancel each other out) so that the sensor can be very sensitive to changes in turbity. On the one hand the bubbles reflect the light so the more bubbles there are the more light reflected from the liquid sample. On the other hand the solid particles scatter or absorb the light so the greater their concentration the less the amount of light which reaches the light sensing means. An increase in the signal from the sensor means more bubbles and/or lees particles, meaning the amount of flocculant should be reduced, and a reduction in the signal means less bubbles and/or more particles meaning the amount of flocculant should be increased.

Thus, a strong response to variations in turbity is obtained allowing close and easy control over the amount of flocculant used, in a manner not readily achieved hitherto with known turbidity meters.

In the method of the invention, bubbles in the liquid constitute an important feature of the measurement system. For this reason de-aeration of the liquid sample is not only unnecessary but it is undesirable, and the elimination of this step in the water purification process is also of benefit.

From the foregoing it will be understood that the invention also resides in a method of purifying water wherein flocculant is added to the water, the water is subsequently centrifuged, the turbidity of the clarified water is determined, and the amount of flocculant being added to the water is adjusted in accordance with the result of the turbidity determination, characterised in that the clarified water is not subjected to de-aeration prior to determination of the turbidity, and the turbidity is determined by the method in accordance with the present invention as maintained above.

The invention also provides a turbidity sensing device suitable for use in putting the method of the invention into practice. The device according to the invention comprises a housing, a chamber in the housing for receiving the liquid, means for emitting light into the liquid in the chamber, and means for sensing light having been emitted by the light emitting means and reflected within the liquid, the light emitting and light sensing means being disposed along an axis, characterised in that the light emitting means is arranged to emit a diffuse light beam into the liquid generally radially of said axis.

In a preferred device according to the invention the light emitting means is a light source and the light sensing means is a photosensor. They are both incorporated in a common sensing unit or probe having a transparent cylindrical side wall providing window portions for light to pass from the light source and to the light sensor, respectively. The probe is slidably mounted in a wall of the housing to enable periodic removal of the probe for cleaning said transparent wall. Preferably the probe is movable, e.g. by being partially removed from the housing, for cleaning and the cleaning is effected automatically by the wiping action of a cleaning element which can conveniently be formed by a seal member sealing the probe to the housing. By this construction a simple operation of occasionally retracting and reinserting the probe is all that is required to maintain the transparent wall clean and free from deposits. Such cleaning operations can be conveniently performed automatically by a driving actuator coupled to the probe and equipped with a timer control, for instance. It is not necessary to interrupt flow of liquid through the turbidity meter as the chamber remains closed throughout the cleaning operation. Because the cleaning operation can be performed frequently and without inconvenience, there is no need to dilute the sample used for measurement, and the drawbacks associated with the strong tendency for lenses to cloud-up in the prior art turbidity meters are averted.

In an especially convenient construction a pair of spaced sealing/cleaning elements are provided and a cleaning solution is contained in the space between these members to assist the cleaning operation.

BRIEF DESCRIPTION OF THE DRAWING

To assist a clear understanding of the invention a turbidity meter embodying the invention is described in more detail below with reference being made to the accompanying drawing which shows the meter in cross-section and in combination with control equipment therefore.

DETAILED DESCRIPTION OF THE DRAWING

Figure 1:
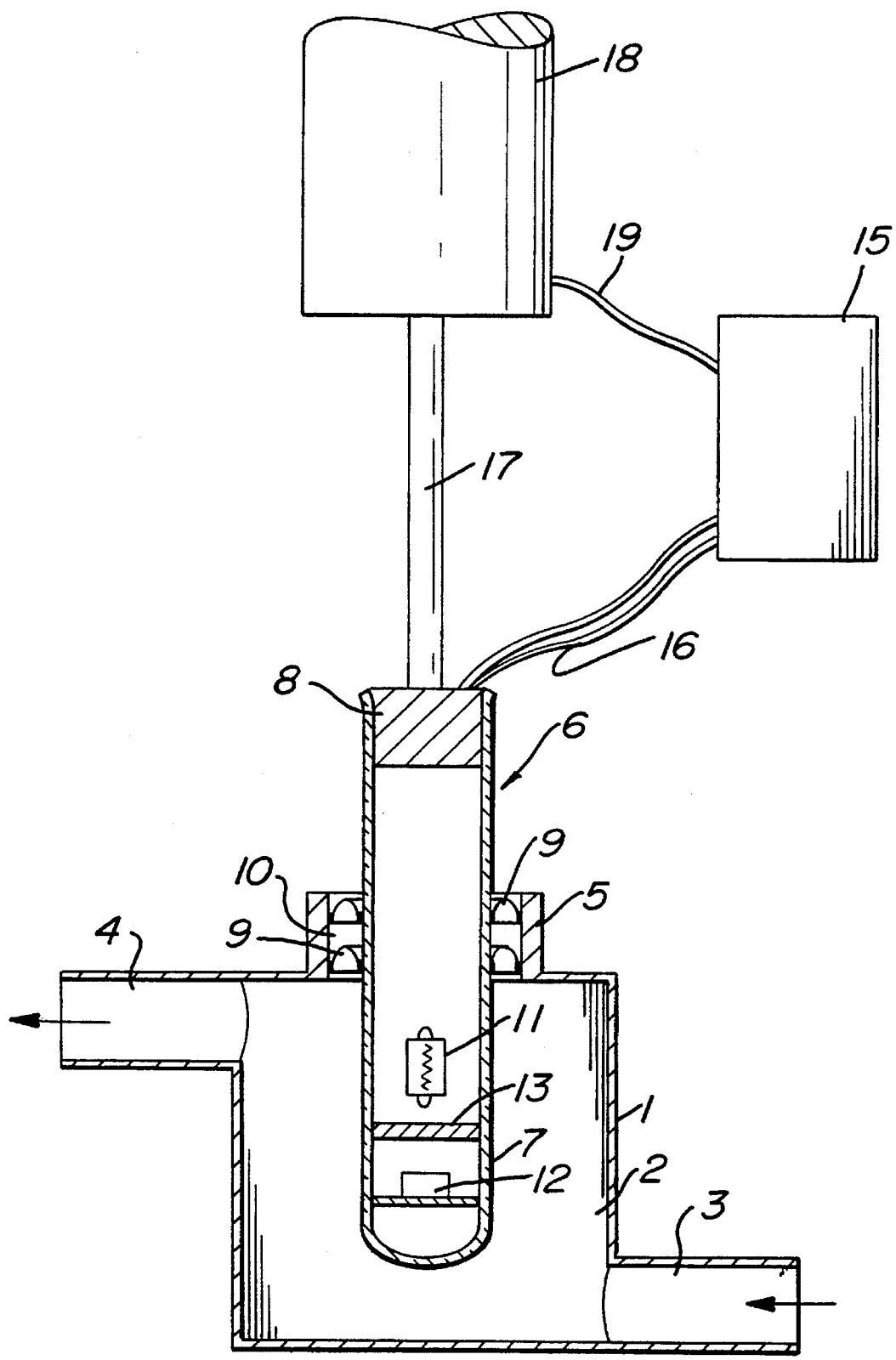

The turbidity meter illustrated in the drawing comprises a housing 1 enclosing a measuring chamber 2. The housing is cylindrical and is provided with a bottom inlet connection 3 and a top outlet connection 4 allowing liquid to stream continuously through the chamber 2. The top wall of the housing has a collar 5 defining a central opening through which a probe 6 passes. As shown the probe comprises a transparent glass tube 7 which is closed at its inner or lower end and is sealed at its upper end by a plug 8 fitted tightly in the tube. The probe 6 is sealed to the housing 1 by a seal arrangement adapted to permit the tube to slide axially into and out of the chamber 2, and to clean the transparent side wall of the tube 7 in response to such displacement of the probe. More particularly the seal arrangement includes a pair of axially spaced apart annular lip seals 9 mounted within the collar 5 and engaging with their free inner edges the tube 7. The seals, tubes and collar enclose a space 10 which is filled with cleaning solution.

Housed within the tube 7 are a light source 11, such as a bulb or other electrical device capable of emitting visible light when energised, and a light sensor 12, such as a photosensitive electrical component. The light source 11 and sensor 12 are separated by an opaque partition 13 extending across the interior of the tube. The partition constitutes a light barrier between the light source 11 and the sensor 12 so that the light emitted by the source must be reflected outside of the tube in order to reach and be detected by the sensor. The light source and the sensor are connected to a control unit 15 by electric leads 16 which enter the probe 6 through the plug 8.

The probe is coupled to the output rod 17 of an electrically driven linear actuator 18 which is connected to the control unit 15 by electric leads 19. The control unit is set to energise the actuator 18, e.g. at selected time intervals, to retract the probe 6 from the housing and then re-insert the probe to its operative position. During such reciprocal displacement of the probe the side wall of the tube 7 is cleaned by the wiping action of the lip seals 9 in conjunction with the cleaning solution contained in the inter-seal space 10.

The probe is withdrawn far enough for the tube portions defining windows surrounding the light source 11 and the sensor 12 to be effectively cleaned, but not so far that the seal between the inner lip seal 9 and the tube 7 is interrupted.

In use of the described turbidity meter liquid, e.g. clarified water discharged from a decanter centrifuge in a water purification plant, flows continuously through the chamber 2 from the inlet 3 to the outlet 4. The light source 11 is energised by the control unit 15 and light radiating from the source passes through the wall of tube 7 into the water. Some of the light is reflected from bubbles in the water and passes back through the tube to be detected by the sensor 12 which produces a signal to the control unit 15 depending on the intensity of the light received. The control unit may include a display providing a visible output of the measured turbidity. Solid particles suspended in the water absorb and scatter the light and as their concentration increases the amount of light detected by the sensor is reduced. The clearer the water the stronger the signal from the sensor, which is also increased by an increase in the number of air bubbles in the water. Consequently, in a water purification plant, the output obtained from turbidity meter is highly responsive to small changes in the properties of the water dependent upon the amount of flocculant added to it and the meter allows accurate control of the flocculant consumption to maintain the consumption at the optimum level. The ideal situation is substantially no solids and little air on the clarified water.

The control 15 can allow the sensitivity of the device to be adjusted, e.g. by varying the power supplied to the light source, to suit the particular application to which the meter is put. Similarly the time interval between cleaning operations may be adjusted according to the nature of the liquid.

When used in an effluent water purification process, the described turbidity meter renders de-aeration and dilution of a liquid sample unnecessary prior to turbidity measurement. Of course the device of the invention can be used in other applications also in which case different widths for the barrier 13 and for the intensity of the source may be appropriate.

Although the particularly described embodiment of the invention has been referred to as a turbidity meter, this should not be taken to mean that it necessarily provides a quantified output of turbidity measurement. For many applications, including that of water purification processes as mentioned, the device of the invention may simply, by suitable arrangement of the control unit, provide a mid-range (or "acceptable") signal when the clarity of the liquid is at the desired level, a reduced signal when the clarity is poorer, and an increased signal when the clarity is even greater. In such cases the device may be regarded to function as a "clarity indicator" rather than a "turbidity meter" within the strict sense of the latter term. Of course, the device can be calibrated to operate as a true turbidity meter should this be required.

The materials used in the described turbidity meter are not critical to its operation. However, by way of example it is mentioned that the seals 9 may be made of rubber, and the cleaning solution, the nature of which will be selected in dependence upon the contaminants to be cleaned from the probe, may be a soap or detergent solution, a solvent or other degreasing agent, or a descaling agent.

I claim:

1. A method of determining the turbidity of a liquid sample containing solid particles and gas bubbles, comprising the steps of: emitting light rays into the liquid sample, detecting the light reflected within the liquid sample and determining the turbidity as a function of the gas bubbles contained within the liquid sample, which vary inversely with the concentration of the solid particles, and the intensity of the light reflected from the gas bubbles.

2. A method according to claim 1, wherein the light is visible light.

3. A method according to claim 2, wherein the light is emitted into the sample as a diffuse beam.

4. A method according to claim 1, wherein the light is emitted into the sample as a diffuse beam.

5. A method according to claim 4, wherein the light is emitted from and detected at respective positions spaced apart along an axis extending through the liquid sample, the light is emitted into the liquid in all radial directions about said axis, and the light is received from the liquid in all radial directions about said axis at the detection position.

6. A method of purifying water containing solid particles and gas bubbles in a continuous process comprising the steps of: adding flocculant to the water, centrifuging the water, determining the turbidity of the centrifuged water, and adjusting the amount of flocculant being added to the water in accordance with the result of the turbidity determination, the turbidity being determined by obtaining a sample of the centrifuged water, emitting light rays into the sample, detecting the reflected light within the sample as a function of the gas bubbles within the sample which varies inversely with the concentration of the solid particles, and the intensity of the light reflected from the gas bubbles.

7. A method of purifying water as claimed in claim 6, wherein the light emitted is visible light.

8. A method of purifying water as claimed in claim 7, wherein the light is emitted into the liquid sample as a diffuse beam.

9. A method of purifying water according to claim 8, wherein the light is emitted from and detected at respective positions spaced apart along an axis extending through the liquid sample, the light is emitted into the liquid in all radial directions about the axis, and the light is detected from the liquid from all radial directions about the axis.

10. A device for determining turbidity of a liquid containing gas bubbles and solids, comprising: a housing, a chamber confined in the housing for receiving the liquid, means for emitting light into the liquid in the chamber, means for detecting light having been emitted by the light emitting means and reflected within the liquid, the light emitting means and light detecting means being located along an axis within a sensing unit, the light emitting means emitting a diffuse light beam into the liquid generally radially around said axis, control means for determining turbidity as a function of the intensity of light emitted and the intensity of light reflected from the gas bubbles and the light not absorbed by the solids into the light detecting means, the housing having an inlet port and an outlet port for the liquid, the ports arranged to cause the liquid to flow continuously over and to immerse the sensing unit in the chamber, the sensing unit having a side wall surrounding said axis and transparent portions for transmitting light into the liquid from the light emitting means and to the detecting means from the liquid, said sensing unit being movably mounted in the housing, and a cleaning element mounted in the housing for wiping clean said transparent wall portions upon movement of the sensing unit relative to the housing.

11. A device according to claim 10, wherein the cleaning element comprises a seal arranged to seal between the sensing unit and the housing.

12. A device according to claim 11, wherein a pair of axially spaced apart seals are provided and confine therebetween a space for holding a cleaning solution.

13. A device according to claim 12, wherein the sensing unit is axially slidable relative to the housing and cleaning element.

14. A device according to claim 12, wherein the sensing unit is axially slidable between a normal and a retracted position to clean the transparent wall portions, and the seal remains in sealing contact with the unit throughout said sliding movement.

15. A device according to claim 11, wherein the sensing unit is axially slidable between a normal and a retracted position to clean the transparent wall portions, and the seal remains in sealing contact with the unit throughout said sliding movement.

16. A device according to claim 15, wherein a driving means is coupled to the sensing unit for axially displacing the unit relative to the housing.

17. A device according to claim 11, wherein the sensing unit is axially slidable relative to the housing and cleaning element.

18. A device according to claim 10, wherein the sensing unit is axially slidable relative to the housing and cleaning element.

19. A device according to claim 18, wherein a driving means is coupled to the sensing unit for axially displacing the unit relative to the housing.

20. A device according to claim 19, wherein a timer control means is connected to the drive means for actuating the drive means at set time intervals to retract and reinsert said unit.

21. A device for determining turbidity of a liquid containing gas bubbles and solids, comprising: a housing enclosing a chamber for receiving the liquid, a unit mounted in a wall of the housing and extending into the chamber, the unit having a transparent window for transmission of light, control means for determining turbidity as a function of the intensity of light emitted and the intensity of light reflected from the gas bubbles and the light not absorbed by the solids into the light detecting means, a sealing member surrounding the unit and in contact with the unit for sealing between the unit and the housing, wherein the unit is movable relative to the housing and the sealing member for cleaning the transparent window by said sealing member wiping over said window.

22. A device according to claim 21, wherein said unit comprises a cylindrical transparent wall defining said window.

23. A device according to claim 22, wherein a pair of spaced sealing members are provided and confine therebetween a space for holding a cleaning solution.

24. A device according to claim 22, wherein a driving means is coupled to the unit and is operable to reciprocate the unit relative to the housing.

25. A device according to claim 21, wherein a pair of spaced sealing members are provided, and confined therebetween is a space for holding a cleaning solution.

26. A device according to claim 25, wherein a driving means is coupled to the unit and is operable to reciprocate the unit relative to the housing.

27. A device according to claim 21, wherein a driving means is coupled to the unit and is operable to reciprocate the unit relative to the housing.

28. A device for determining turbidity of a liquid containing gas bubbles and solids, comprising a housing, a chamber confined in the housing for receiving the liquid, means for emitting light into the liquid in the chamber, means for detecting light having been emitted by the light emitting means and reflected within the liquid, the light emitting means and light detecting means being located along an axis within a sensing unit, the light emitting means being a light source and emitting a diffuse light beam into the liquid generally radially around said axis, the light detecting means being a photosensor, control means for determining turbidity as a function of the intensity of light emitted and the intensity of light reflected from the gas bubbles and the light not absorbed by the solids into the light detecting means, the housing having an inlet port and an outlet port for the liquid, the ports arranged to cause the liquid to flow continuously over and to immerse the sensing unit in the chamber, the sensing unit having a cylindrical side wall surrounding said axis and transparent portions for transmitting light into the liquid from the light emitting means and to the detecting means from the liquid, the light emitting means and the light detecting means being optically isolated from each other in the sensing unit by an opaque barrier, said sensing unit being movably mounted in the housing, and a cleaning element mounted in the housing for wiping clean said transparent wall portions upon movement of the sensing unit relative to the housing.

29. A device for determining turbidity of a liquid containing gas bubbles and solids, comprising a housing, a chamber confined in the housing for receiving the liquid, means for emitting light into the liquid in the chamber, means for detecting light having been emitted by the light emitting means and reflected within the liquid, the light emitting means and light detecting means being located along an axis within a sensing unit, the light emitting means being a light source and emitting a diffuse light beam into the liquid generally radially around said axis, the light detecting means being a photosensor, control means for determining turbidity as a function of the intensity of light emitted and the intensity of light reflected from the gas bubbles and the light not absorbed by the solids into the light detecting means, the housing having an inlet port and an outlet port for the liquid, the ports arranged to cause the liquid to flow continuously over and to immerse the sensing unit in the chamber, the sensing unit having a side wall surrounding said axis and transparent portions for transmitting light into the liquid from the light emitting means and to the detecting means from the liquid, the light emitting means and the light detecting means being optically isolated from each other in the sensing unit by an opaque barrier, said sensing unit being movably mounted in the housing, and a cleaning element mounted in the housing for wiping clean said transparent wall portions upon movement of the sensing unit relative to the housing.

* * * * *